(12) United States Patent
Tan

(10) Patent No.: US 8,648,192 B2
(45) Date of Patent: Feb. 11, 2014

(54) 2-OXO-1,2-DIHYDROPYRIDIN-4-YLBORONIC ACID DERIVATIVES

(75) Inventor: Zhulin Tan, Cheshire, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/697,862

(22) PCT Filed: May 23, 2011

(86) PCT No.: PCT/US2011/037525
§ 371 (c)(1),
(2), (4) Date: Nov. 29, 2012

(87) PCT Pub. No.: WO2011/149822
PCT Pub. Date: Dec. 1, 2011

(65) Prior Publication Data
US 2013/0203985 A1   Aug. 8, 2013

Related U.S. Application Data

(60) Provisional application No. 61/348,384, filed on May 26, 2010.

(51) Int. Cl.
*C07F 5/02* (2006.01)
(52) U.S. Cl.
USPC .......................................................... 546/13
(58) Field of Classification Search
None
See application file for complete search history.

(56) References Cited

U.S. PATENT DOCUMENTS

| | | | |
|---|---|---|---|
| 3,681,349 | A | 8/1972 | Schwan et al. |
| 5,776,959 | A | 7/1998 | Covey et al. |
| 5,811,422 | A | 9/1998 | Lam et al. |
| 8,114,868 | B2 | 2/2012 | Himmelsbach |
| 8,202,857 | B2 | 6/2012 | Claremon et al. |
| 8,242,111 | B2 | 8/2012 | Claremon et al. |
| 2007/0208001 | A1 | 9/2007 | Zhuo et al. |
| 2009/0264650 | A1 | 10/2009 | Cho et al. |
| 2010/0016164 | A1 | 1/2010 | Hino et al. |
| 2010/0041637 | A1 | 2/2010 | Claremon et al. |
| 2010/0197675 | A1 | 8/2010 | Claremon et al. |
| 2010/0256363 | A1 | 10/2010 | Xu |
| 2010/0324045 | A1 | 12/2010 | Claremon et al. |
| 2010/0331320 | A1 | 12/2010 | Renz et al. |
| 2011/0009402 | A1 | 1/2011 | Himmelsbach |
| 2011/0015157 | A1 | 1/2011 | Claremon et al. |
| 2011/0021512 | A1 | 1/2011 | Claremon et al. |
| 2011/0034455 | A1 | 2/2011 | Claremon et al. |
| 2011/0053943 | A1 | 3/2011 | Claremon et al. |
| 2011/0071139 | A1 | 3/2011 | Claremon et al. |
| 2011/0098320 | A1 | 4/2011 | Claremon et al. |
| 2011/0105504 | A1 | 5/2011 | Claremon et al. |
| 2011/0112062 | A1 | 5/2011 | Claremon et al. |
| 2011/0112082 | A1 | 5/2011 | Claremon et al. |
| 2011/0124635 | A1 | 5/2011 | Claremon et al. |
| 2011/0136821 | A1 | 6/2011 | Claremon et al. |
| 2011/0190262 | A1 | 8/2011 | Himmelsbach et al. |
| 2011/0263582 | A1 | 10/2011 | Claremon et al. |
| 2011/0263583 | A1 | 10/2011 | Claremon et al. |
| 2011/0263584 | A1 | 10/2011 | Claremon et al. |
| 2011/0269957 | A1 | 11/2011 | Fandrick et al. |
| 2011/0312950 | A1 | 12/2011 | Eckhardt et al. |
| 2012/0040973 | A1 | 2/2012 | Claremon et al. |
| 2012/0108578 | A1 | 5/2012 | Himmelsbach et al. |
| 2012/0184549 | A1 | 7/2012 | Himmelsbach |
| 2012/0190675 | A1 | 7/2012 | Himmelsbach |
| 2012/0208804 | A1 | 8/2012 | Claremon et al. |
| 2012/0232050 | A1 | 9/2012 | Claremon et al. |
| 2012/0277149 | A1 | 11/2012 | Hamilton et al. |
| 2012/0277455 | A1 | 11/2012 | Qu et al. |

FOREIGN PATENT DOCUMENTS

| | | |
|---|---|---|
| DE | 10034623 A1 | 1/2002 |
| EP | 0645387 A1 | 3/1995 |
| EP | 0928789 A1 | 7/1999 |
| EP | 1156049 A1 | 11/2001 |
| EP | 1801098 A1 | 6/2007 |
| EP | 1852425 A1 | 11/2007 |
| EP | 1864971 A1 | 12/2007 |
| JP | 2007254409 A | 10/2007 |
| WO | 9614297 A1 | 5/1996 |

(Continued)

OTHER PUBLICATIONS

Abstract in English for DE10034623, Publication Date Jan. 31, 2002.
Aluri, B.R. et al., "Bulky n-Substituted 1,3-Benzazaphospholes: Access via Pd-Catalyzed C—N and C—P Cross Coupling, Lithiation, and Conversion to Novel P=C PtBu2 Hybrid Ligands". Inorganic Chemistry, 2008, 47, p. 6900-6912.
Aluri, B.R. et al., "Sterically and Polarity-Controlled Reactions of tBuLi with P=CH—NR Heterocycles: Novel Heterocyclic P-and P,O-Ligands and Preliminary Tests in Transition-Metal Catalysis", Chem. Eur. Journal, vol. 14, 2008, p. 4328-4335.

(Continued)

*Primary Examiner* — Janet L Andres
*Assistant Examiner* — Heidi Reese
(74) *Attorney, Agent, or Firm* — Michael P. Morris; David L. Kershner

(57) ABSTRACT

The present invention relates to a compound of formula (I) wherein $R^1$, $R^2$ and n are as defined herein. The invention also relates to processes for making the compounds of formula (I) and methods of using the compounds of formula (I) as reagents in organic synthesis.

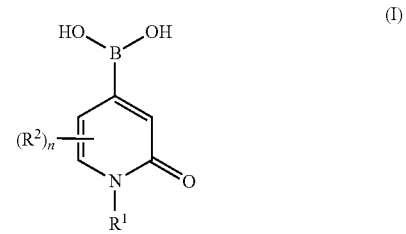

(I)

11 Claims, No Drawings

(56) References Cited

FOREIGN PATENT DOCUMENTS

| | | |
|---|---|---|
| WO | 0009107 A2 | 2/2000 |
| WO | 0113917 A1 | 3/2001 |
| WO | 0144200 A2 | 6/2001 |
| WO | 03057673 A1 | 7/2003 |
| WO | 2004056745 A2 | 7/2004 |
| WO | 2004094375 A2 | 11/2004 |
| WO | 2005108361 A1 | 11/2005 |
| WO | 2005116002 A2 | 12/2005 |
| WO | 2006002349 A1 | 1/2006 |
| WO | 2006014357 A1 | 2/2006 |
| WO | 2006017443 A2 | 2/2006 |
| WO | 2006024627 A2 | 3/2006 |
| WO | 2006024628 A1 | 3/2006 |
| WO | 2006031715 A2 | 3/2006 |
| WO | 2006040329 A1 | 4/2006 |
| WO | 2006049952 A1 | 5/2006 |
| WO | 2006104280 A1 | 10/2006 |
| WO | 2007061661 A2 | 5/2007 |
| WO | 2007081570 A2 | 7/2007 |
| WO | 2007101270 A1 | 9/2007 |
| WO | 2007103719 A2 | 9/2007 |
| WO | 2007124254 A2 | 11/2007 |
| WO | 2007124329 A1 | 11/2007 |
| WO | 2007124337 A1 | 11/2007 |
| WO | 2007127693 A1 | 11/2007 |
| WO | 2007127763 A2 | 11/2007 |
| WO | 2008024497 A2 | 2/2008 |
| WO | 2008046758 A2 | 4/2008 |
| WO | 2008059948 A1 | 5/2008 |
| WO | 2008106128 A2 | 9/2008 |
| WO | 2009017664 A1 | 2/2009 |
| WO | 2009017671 A1 | 2/2009 |
| WO | 2009020140 A1 | 2/2009 |
| WO | 2009061498 A1 | 5/2009 |
| WO | 2009075835 A1 | 6/2009 |
| WO | 2009088997 A1 | 7/2009 |
| WO | 2009094169 A1 | 7/2009 |
| WO | 2009102428 A2 | 8/2009 |
| WO | 2009102460 A2 | 8/2009 |
| WO | 2009108332 A1 | 9/2009 |
| WO | 2009117109 A1 | 9/2009 |
| WO | 2009131669 A2 | 10/2009 |
| WO | 2009134384 A1 | 11/2009 |
| WO | 2009134387 A1 | 11/2009 |
| WO | 2009134392 A1 | 11/2009 |
| WO | 2009134400 A1 | 11/2009 |
| WO | 2010010150 A1 | 1/2010 |
| WO | 2010010157 A2 | 1/2010 |
| WO | 2010011314 A1 | 1/2010 |
| WO | 2010089303 A1 | 8/2010 |
| WO | 2010091067 A2 | 8/2010 |
| WO | 2010104830 A1 | 9/2010 |
| WO | 2010127237 A2 | 11/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

ChemAbstract—Accession #: 1969:68280. Maillard, J. et al., "Spiroheterocyclic cycloalkane compounds II. Synthesis of 6-substituted-tetrahydro-2H-1, 3-oxazine-2-ones." Chima Therapeutica, 3(5), 1968, pp. 321-324.

ChemAbstract—Accession #: 1978:563520. Slyusarenko, E.I., et al., Syntheses based on thionylamides. IV. 2-alkoxy-5,6-dihydro-1,3-oxazines. Zhurnal Organicheskoi Chimii, 14(5), 1979, p. 1093.

ChemAbstract—Accession #: 1983:595067. Saitkulova, F.G. et al., "Syntheses involving bromozinc alcholates of carboxylic acid esters". Khimiya Elementoorganicheskikh Soedinii, vol. 1982, 1982, pp. 22-26.

ChemAbstract—Accession #: 1983:89280. Lapkin, I.I. et al., "Synthesis of 1,3-oxazine-2,4-diones." Zhurnal Organicheskoi Khimii, vol. 18, No. 11, 1982, p. 2468.

ChemAbstract—Accession No. 2007:1110441 Abstract, Chemical Abstract Service, Columbus, Ohio, Fukushima, H. et al., "Preparation of imidazolidinone derivatives as 11.beta.-HSD1 inhibitors". JP2007254409 (Taisho Pharmaceutical Co. Ltd., Japan, Oct. 4, 2007. (Attached is a machine translation of the ChemAbstract and a Derwent World Patents Index file record).

ChemAbstract: CAS: 150:214405, Accession #: 2009:140024. Claremon, D.A., et al., Preparation of 1,3-oxazinan-2-one dervatives as inhibitors of 11-beta-hydroxysteroid dehydrogenase type1. 2009.

Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.

Evans, B.E. et al., "Orally active, nonpeptide osytocin antagonists". Journal of Medicinal Chemistry, American Chem. Soc., Vo. 35, No. 21, Oct. 15, 1992, p. 3919-3927.

Fandrick, D.R. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.

Goubet, F. et al., "Conversion of a Thiohydantoin to the Corresponding Hydantoin via a Ring-Opening/Ring Closure Mechanism". Tetrahedron Letters, Elsevier, Amsterdam, vol. 37. No. 43, Oct. 21, 1996. p. 7727-7730.

Harno, E. et al., "Will treating diabetes with 11-beta-HSD1 inhibitors affect the HPA axis?" Trends in Endocrinology and Metabolism, Elsevier Science Publishing, NY, NY, USm, vol. 21, No. 10, Oct. 1, 2010, pp. 619-627.

Kashima, C. et al., "Preparation of N-Aryl-2,4-diaminopentanes by the Ring Opening Reaction of 1-Aryl-3,4,5,6-tetradydro-2-(1H)pyrimidinones". Journal of Heterocyclic Chemistry, vol. 18, 1981, p. 1595-1596.

Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.

Muehlstadt, M. et al., "Cyclisation reactions of beta,gamma-unsaturated derivatives of carbonis acid. IX" Journal Fuer Praktische Chemi, vol. 328, 1986, p. 163-172.

Rosenstock, J. et al., "The 11-beta-hydroxysteroid Dehydrogenase Type 1 inhibitor INCB13739 Improves Hyperglycemia in Patients with Type 2 Diabetes Inadequately Controlled by Metformin Monotherapy." Diabetes Care, vol. 33, No. 7, Jul. 2010, pp. 1516-1522.

Schoellkopf, U. et al., "Umsetzungen Alphametallierter Isocyanide Mit Eigigen 1,3-Dipolen" English: "Reactions of alpha-metalated osicyanidews with some 1,3-dipoles", Liebigs Annalen Der Chemie, Verlag Chemi, GmbH, Weinheim, DE, vol. 4, Jan. 1, 1980, p. 600-610.

Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.

Shibata, I. et al., "Cycloaddition of Oxetanes with Heterocumulenes Catalyzed by Organotin Iodine-Lewis Base Complex". Journal of Heterocyclic Chemistry, vol. 24, 1987, p. 361-363.

Tadayyon M. et al., "Insulin sensitisation in the treatment of Type 2 diabetes." Expert Opinion on Investigational Drugs, Ashley Publications, Ltd., London, GB, vol. 12, n. 3, Mar. 1, 2003, pp. 307-324.

Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.

Tamaru, Y. et al., "Urea as the Most Reactive and Versatile Nitrogen Nucleophile for the Palladium (2+)-Catalyzed Cyclization of Unsaturated Amines," J. Am. Chem. Soc., 1988, 110, 3994-4002.

(56) References Cited

OTHER PUBLICATIONS

Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.

Worthy, A.D. et al., "Regioselective Hydroformylation of Sulfonamides using a Scaffolding Ligand". Organic Letters, 2009, vol. 11, No. 13—p. 2764-2767.

2-OXO-1,2-DIHYDROPYRIDIN-4-YLBORONIC ACID DERIVATIVES

FIELD OF THE INVENTION

The invention relates to 2-oxo-1,2-dihydropyridin-4-ylboronic acid derivatives, methods of making these compounds, and their use in chemical processes.

BACKGROUND OF THE INVENTION

The Suzuki coupling reaction provides an efficient process for joining arenes (aryls and/or heteroaryls) in the presence of a palladium catalyst (see, e.g., N. Miyaura et al., *Synthetic Communications* 11: 7, 51-519 (1981); and N. Miyaura et al. *Chem. Rev.* 95: 2457-2483 (1995). In the Suzuki reaction, a haloarene is reacted with an areneboronic acid in the presence of Pd catalyst and base to form a biarene product. The reaction can also be carried out using areneboronic esters instead of areneborate acids.

WO2009074812 describes a Suzuki couplings using an areneborate ester, that is, 1-methyl-4-(4,4,5,5-tetramethyl-1,3,2-dioxaborolan-2-yl)pyridin-2(1H)-one. WO2009/017664, WO2009/134400, WO2009/017671, and WO2010/011314 also describe Suzuki couplings using areneborate esters including pyridylborate esters to prepare compounds useful for treating metabolic disorders such as diabetes.

WO2009/017664, WO2009/134400, WO2009/017671, and WO2010/011314 describe Suzuki coupling reactions using a reagent of formula $(HO)_2B\text{-}Cy^2$, where Cy is described as aryl, heteroaryl, cycloalkyl or heterocyclyl. The references also describe compounds where Cy is pyridine and oxo-pyridine.

However, Applicants are unaware of any 2-oxo-1,2-dihydropyridin-4-ylboronic acid derivative where the pyridine nitrogen atom is substituted by an alkyl or cycloalkyl. Such compounds are useful for making compounds in which a 2-oxo-1,2-dihydropyridine derivative is coupled to an aryl or heteroaryl ring at the 4-position of the pyridine.

BRIEF SUMMARY OF THE INVENTION

In its broadest embodiment the invention relates to 1-alkyl- and 1-cycloalkyl-2-oxo-1,2-dihydropyridin-4-ylboronic acid derivatives of formula (I):

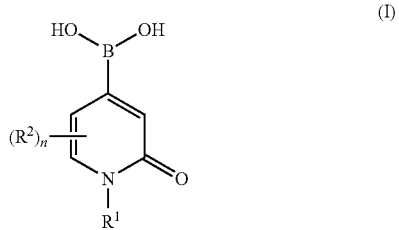

(I)

wherein:

n is 0, 1, 2 or 3;

$R^1$ is —$(C_1\text{-}C_6)$alkyl or —$(C_3\text{-}C_6)$cycloalkyl; wherein said —$(C_1\text{-}C_6)$alkyl and —$(C_3\text{-}C_6)$cycloalkyl may be optionally substituted with one to three groups independently selected from —$(C_1\text{-}C_6)$alkyl, —$O(C_1\text{-}C_6)$alkyl, halo, —$NH_2$, —NH$(C_1\text{-}C_6)$alkyl, —$N((C_1\text{-}C_6)$alky)$l_2$, and —CN; and each $R^2$ is independently selected from —$(C_1\text{-}C_6)$alkyl, —$O(C_1\text{-}C_6)$alkyl, —$(C_3\text{-}C_6)$cycloalkyl, halo, —$NH_2$, —NH$(C_1\text{-}C_6)$alkyl, —$N((C_1\text{-}C_6)$alky)$l_2$, and —CN.

In one embodiment, the invention relates to a compound of formula (I) wherein $R^1$ is —$(C_1\text{-}C_6)$alkyl.

In another embodiment, the invention relates to a compound of formula (I) wherein $R^1$ is methyl.

In one embodiment, the invention relates to a compound of formula (I) wherein $R^1$ is —$(C_3\text{-}C_6)$cycloalkyl.

In another embodiment, the invention relates to a compound of formula (I) wherein $R^1$ is cyclopropyl.

In another embodiment, the invention relates to any of the preceding embodiments wherein n is 0.

In another embodiment, the invention relates to a compound of formula (I) wherein $R^1$ is methyl and n is 0.

In another embodiment, the invention relates to a compound of formula (I) wherein $R^1$ is cyclopropyl and n is 0.

The invention also relates to methods of making the compounds of formula (I) and the use of compounds of formula (I) as reagents in chemical synthesis, e.g., in Suzuki couplings.

DETAILED DESCRIPTION OF THE INVENTION

The term "—$(C_1\text{-}C_6)$alkyl" refers to branched and unbranched alkyl groups having from 1 to 6 carbon atoms. Examples of —$(C_1\text{-}C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the —$(C_1\text{-}C_6)$alkyl group can be the point of attachment to another group or moiety.

The term "—$(C_3\text{-}C_6)$cycloalkyl" refers to a nonaromatic 3- to 6-membered monocyclic carbocyclic radical. Examples of "—$(C_3\text{-}C_6)$cycloalkyls include cyclopropyl, cyclobutyl, cyclohexyl, cyclopentyl and cyclohexyl.

The term "$C_{6\text{-}10}$ aryl" refers to aromatic hydrocarbon rings containing from six to ten carbon ring atoms. The term $C_{6\text{-}10}$ aryl includes monocyclic rings and bicyclic rings where at least one of the rings is aromatic. Non-limiting examples of $C_{6\text{-}10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heteroaryl" refers to an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "arene" refers to a $C_{6\text{-}10}$ aryl or 5 to 11-membered heteroaryl.

The terms "haloarene" and "trifluoromethanesulfonyloxyarene" refer to a $C_{6\text{-}10}$ aryl or 5 to 11-membered heteroaryl containing at least one halogen (haloarene) or trifluoromethanesulfonyloxyarene (trifluoromethanesulfonyloxyarene) bonded to an arene carbon ring atom. It will be understood that the haloarene or trifluoromethanesulfonyloxyarene may be a moiety that is part of a larger molecule such as described in WO2009/017664, WO2009/134400, WO2009/017671, and WO2010/

011314, the content of each of the foregoing being incorporated by reference in its entirety.

The term "halo" or "halogen" refers to fluoro, chloro, bromo or iodo.

As noted above, the invention also relates to compounds of formula (I) and methods of making the compounds of formula (I). A nonlimiting method of making the compounds of formula (I) is depicted below in Scheme 1.

Scheme 1

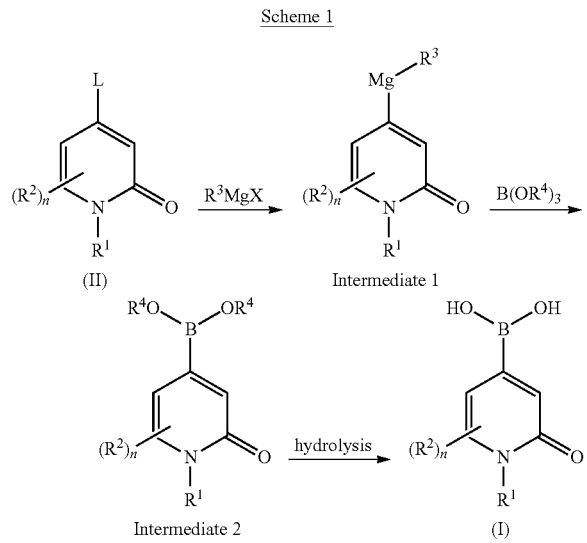

Intermediate 1

Intermediate 2          (I)

Accordingly, in one embodiment, the invention relates to a method of making the compounds of formula (I) as depicted in Scheme 1 comprising:

allowing a compound of formula (II) to react with a Grignard reagent to form a first intermediate ("Intermediate 1");

allowing the first intermediate to react with an alkylborate to form a second intermediate ("Intermediate 2");

and hydrolyzing the second intermediate ("the hydrolyzing step") to provide the compound of formula (I); wherein $R^1$, $R^2$ and n are as defined above for the compound of formula (I);

$R^3$ and $R^4$ are each independently a —$(C_1$-$C_6)$alkyl;

L is a leaving group selected from halo and trifluoromethanesulfonyloxy; and

X is a chloro, bromo, or iodo.

In one embodiment, the invention relates to a method of making the compound of formula (I) in the embodiment described above, wherein L is bromo.

In another embodiment, the invention relates to a method of making the compound of formula (I) in any of the embodiments described above, wherein n is 0.

In another embodiment, the invention relates to a method of making the compound of formula (I) in any of the embodiments described above, wherein $R^1$ is methyl or cyclopropyl.

In another embodiment, the invention relates to a method of making the compound of formula (I) as described in the broadest embodiment above, wherein L is bromo or chloro; n is 0, and $R^1$ is methyl.

In another embodiment, the invention relates to a method of making the compound of formula (I) as described in the broadest embodiment above, wherein L is bromo or chloro; n is 0, and $R^1$ is cyclopropyl.

In another embodiment, the invention relates to a method of making the compound of formula (I) as described in all the embodiments above, wherein $R^3$ is a branch-chain —$(C_1$-$C_6)$ alkyl.

In another embodiment, the invention relates to a method of making the compound of formula (I) as described in all the embodiments above, wherein $R^3$ is isopropyl.

In another embodiment, the invention relates to a method of making the compound of formula (I) as described in all the embodiments above, wherein $R^4$ is a straight-chain —$(C_1$-$C_6)$alkyl.

In another embodiment, the invention relates to a method of making the compound of formula (I) as described in all the embodiments above, wherein $R^4$ is methyl.

As depicted in Scheme 1, reaction of the Grignard reagent with the compound of formula (I) forms Intermediate 1. The Grignard reaction step used to form Intermediate 1 is carried out under anhydrous conditions in an ethereal solvent such as, e.g., diethyl ether, diisopropyl ether, methyl t-butlyl ether, tetrahydrofuran (THF), dioxane, and combinations thereof. A preferred solvent for the Grignard reaction step is tetrahydrofuran.

Nonlimiting examples of useful Grignard reagents include alkyl magnesium halides, e.g., isopropylmagnesium chloride. The reaction with the Grignard reagent is carried out for a time and at a temperature sufficient to allow substantially all of the Grignard reagent to react with the compound of formula (I). In one embodiment, a suitable temperature is from about −30° C. to about 50° C.; in another embodiment, from about −30° C. to about 0° C.; and in another embodiment, from about −25° C. to about 0° C.

In one embodiment, a suitable time for reacting the Grignard reagent with the compound of formula (I) is from about 0.25 hours to about 48 hours; in another embodiment, from about 1 hour to about 24 hours; and in another embodiment, from about 1 hour to about 12 hours. It will be understood that the above reaction times also includes the time required to contact the Grignard reagent with compound of formula (I).

The reaction of Intermediate 1 with the alkylborate is typically carried out by adding the alkylborate portion-wise to the first intermediate. The alkylborate can be added neat (i.e., without further dissolution in a solvent) or as a solution. When used as a solution, the solvent is typically the same solvent as used during reaction of the Grignard reagent with the compound of formula (II) (e.g., an etheral solvent).

The reaction of Intermediate 1 with the alkylborate is carried out for a time and at a temperature sufficient to allow substantially all of Intermediate 1 to react with the alkyl borate. In one embodiment, a suitable temperature is from about −30° C. to about 50° C.; in another embodiment, from about −30° C. to about 0° C.; and in another embodiment, from about −25° C. to about 0° C.

In one embodiment, a suitable time for reacting the alkyl borate with Intermediate 1 is from about 0.25 hours to about 48 hours; in another embodiment, from about 0.5 hours to about 24 hours; and in another embodiment, from about 0.5 hours to about 12 hours. It will be understood that the above reaction times also includes the time required to contact the alkyl borate with Intermediate 1.

Intermediate 2 is then hydrolyzed ("the hydrolysis step") under conditions sufficient to convert Intermediate 2 into the compound of formula (I). The hydrolysis step can be carried out under acidic, neutral or basic conditions. Typically, the hydrolysis step is carried out under acidic conditions at a temperature of from about 0° C. to about 50° C.; more typically at a temperature of from about 0° C. to about 30° C.

After hydrolysis the compound of formula (I) is separated from the reaction mixture, purified, and dried using methods known in the art. For example, when the compound of formula (I) formed in the hydrolysis step is a solid, then the solid can be separated from the liquid phase by filtration or decantation. The solids can then be washed with a suitable solvent and dried. If desired, additional compound of formula (I) may be recovered from the liquid phase and/or solvent washes.

The compound of formula (II) is commercially available or can be made by methods known in the art (see, e.g., WO2010043396, WO2010025890, WO2010010157, WO2009134400, WO2009074812, WO2009033703, WO2009033704, WO2008107479, WO2007104783, WO2005007644, WO2006017443, and references cited therein).

As noted above, the compounds of formula (I) are useful reagents in Suzuki coupling reactions. For example, the compound of formula (I) can be reacted with a haloarene or trifluoromethanesulfonyloxyarene to form the corresponding pyridin-4-yl-2-oxo of formula (IV) as depicted below in Scheme 2.

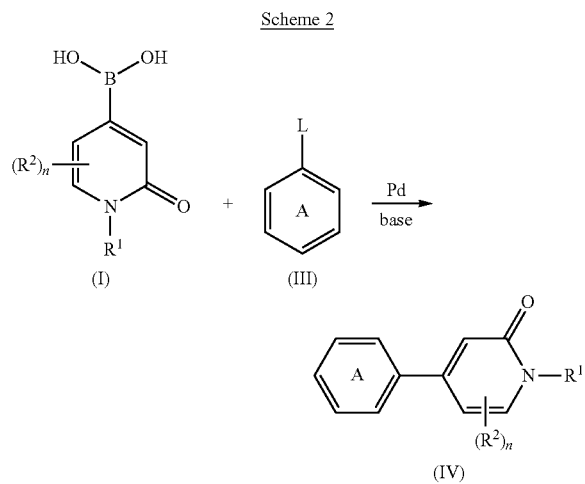

Scheme 2

As depicted in Scheme 2, the compound of formula (I) is reacted with a compound of formula (III) which is an arene substituted with a leaving group L. (The arene ring shown in Scheme 2 is depicted as 6-membered ring A for clarity.) The reaction is carried out in the presence of a palladium catalyst (e.g., $PdCl_2(dppf)$) and base (e.g., $Na_2CO_3$) to provide the compound of formula (IV).

The leaving group (L) depicted in the compound of formula (III) is a group that can be displaced by the boric acid moiety of the compound of formula (I). Nonlimiting examples of leaving groups (L) include halo (chloro, bromo, or iodo) and trifluoromethanesulfonyloxy. In a preferred embodiment, L is bromo or chloro.

In one embodiment, the compound of formula (III) is a haloarene or trifluoromethanesulfonyloxyarene.

In a preferred embodiment, the compound of formula (III) is a haloarene or trifluoromethanesulfonyloxyarene as disclosed in WO2009/017664, WO2009/134400, WO2009/017671, and WO2010/011314.

Nonlimiting examples of palladium catalysts useful for carrying out the coupling reaction depicted in Scheme 2 include [1,1'-bis(diphenylphosphino)ferroncene]dichloropalladium(II), tetrakis(triphenylphospine)palladium(0) (Pd(Ph$_3$)$_4$), palladium acetate (Pd(OAc)$_2$), tris(dibenzylideneacetone)dipalladium(0), palladium on charcoal, and combinations thereof.

In one embodiment, the invention relates to a method of making a compound of formula (IV) as depicted in Scheme 2 above comprising:

allowing a compound of formula (III) to react with a compound of formula (I) in the presence of a palladium catalyst and base.

In one embodiment, the invention relates to a method of making the compound of formula (IV) as described in the embodiment above, wherein L is bromo or chloro.

In another embodiment, the invention relates to a method of making the compound of formula (IV) as described in any of the embodiments above, wherein n is 0.

In another embodiment, the invention relates to a method of making the compound of formula (IV) as described in any of the embodiments above, wherein $R^1$ is methyl or cycloalkyl.

In another embodiment, the invention relates to a method of making the compound of formula (IV) as described in any of the embodiments above, wherein the palladium catalyst is [1,1'-bis(diphenylphosphino)ferroncene]dichloropalladium (II), complex with dichloromethane.

In another embodiment, the invention relates to a method of making the compound of formula (IV) as described in any of the embodiments above, wherein the compound of formula (III) is (S)-3-((S)-1-(4-bromophenyl)ethyl)-6-(2-hydroxy-2-methylpropyl)-6-phenyl-1,3-oxazinan-2-one, or a hydrate thereof.

In another embodiment, the invention relates to a method of making the compound of formula (IV) as described in any of the embodiments above, wherein the compound of formula (III) is (S)-3-((S)-1-(4-bromophenyl)ethyl)-6-(2-hydroxy-2-methylpropyl)-6-phenyl-1,3-oxazinan-2-one is a monohydrate.

In another embodiment, the invention relates to a method of making the compound of formula (IV) as described as described second embodiment immediately above, wherein the compound of formula (III) is (S)-3-((S)-1-(4-bromophenyl)ethyl)-6-(2-hydroxy-2-methylpropyl)-6-phenyl-1,3-oxazinan-2-one in the form of a nonsolvate.

EXAMPLES

The following HPLC conditions are used to determine the purity of Compound 1 prepared in Example 1:

Column: Halo C18 (MAC-MOD Analytical, Inc. No. 92814-702, s/n AH072246). 4.6×150 mm. Particle size 2.7 µm.

Mobile phase A: water with 0.05% (v/v) phosphoric acid.

Mobile phase B: acetonitrile with 0.05% (v/v) phosphoric acid.

Gradient: 5% mobile phase B to 95% mobile phase B in 7 min; held at 95% mobile phase B for 3 min.

Runtime: 10 minutes with a post run of 2 min.

Flow rate: 1.20 mL/min.

Temperature: 25° C.

Injection: 2.0 µl.

UV detector: 220 nm, bandwidth 8 nm; ref 500 nm, bandwidth 100 nm.

Example 1

Synthesis of 1-methyl-2-oxo-1,2-dihydropyridin-4-ylboronic acid (1). Compound 1 is prepared using the procedure depicted in Scheme 3 and described below.

Scheme 3

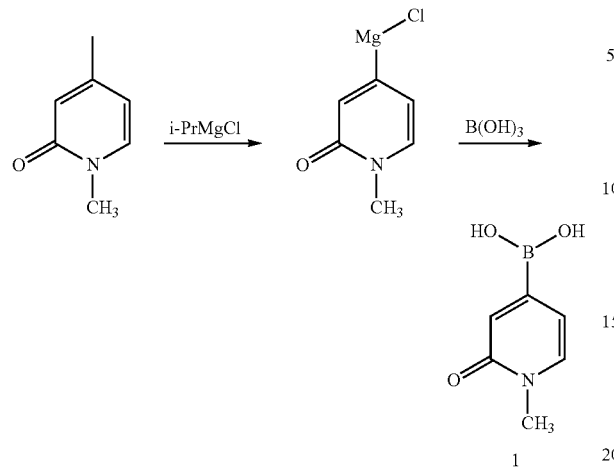

Step 1. A solution of isopropylmagnesium chloride (175 mL, 1.85 M in THF, 0.32 mol, 1.54 eq.) is charged to a 500-mL jacketed reactor under nitrogen atmosphere with mechanical agitation. The contents of the reactor are cooled to −18° C. and treated with a solution of 4-bromo-1-methylpyridine-2(1H)-one (40.0 g, 0.21 mol, 1.00 eq.) over about 1 hour. The rate of addition is controlled to maintain a reaction temperature of no higher than −15° C. The contents of the reactor are warmed to −10° C., mixed for 1 hour, and warmed to 20° C.

Step 2. The contents of the reactor from Step 1 are cooled to −20° C. and treated with neat trimethylborate (38 mL, 0.36 mol, 1.62 eq.) at a rate sufficiently slow (approximately 1 hour) to keep the batch temperature at or below −15° C. The contents of the reactor are then warmed to −10° C., mixed for 1 hour, and warmed to 20° C.

Step 3. Hydrochloric acid (140 mL, 2.56 N, 0.36 mol, 1.70 eq.) is cooled to about 5° C. and treated with the reaction mixture from Step 2. The rate of addition is slow enough to maintain a reaction temperature of less than 25° C. The contents of the reactor are then mixed at 20° C. for 6 hours. The resultant solids are collected by filtration, washed with isopropyl acetate (50 mL), and dried under reduced pressure at 21° C. to provide a first crop of 1 as a white crystalline solid. Yield: 14.72 g, 42%. Purity: 98.9 A % by HPLC (220 nm); 91.7 wt % by $^1$H NMR.

$^1$H NMR (DMSO-d6, 500 MHz) δ 8.37 (brs, 2H), 7.59 (d, J=6.60 Hz, 1H), 6.78 (s, 1H), 6.40 (d, J=6.55 Hz, 1H), 3.40 (s, 3H).

MS (ES) m/z=154 [M+H]$^+$.

A second batch of product is collected by reducing the volume of the filtrate under reduced pressure, adding isopropyl acetate (200 mL) at 21° C. to the concentrated solution, and mixing the resultant slurry for 2 hours. The resultant solids are collected by filtration, washed with isopropyl acetate (50 mL) and dried under reduced pressure at 21° C. to provide a second crop of 1 as a white solid. Yield: 10.42 g, 28%. Purity: 98.0 A % by HPLC (220 nm); 85.6 wt % by $^1$H NMR.

Total yield based on both crops of 1: 70%.

Example 2

Synthesis of (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one monohydrate (2) Compound 2 is prepared using the procedure depicted in Scheme 4 and described below.

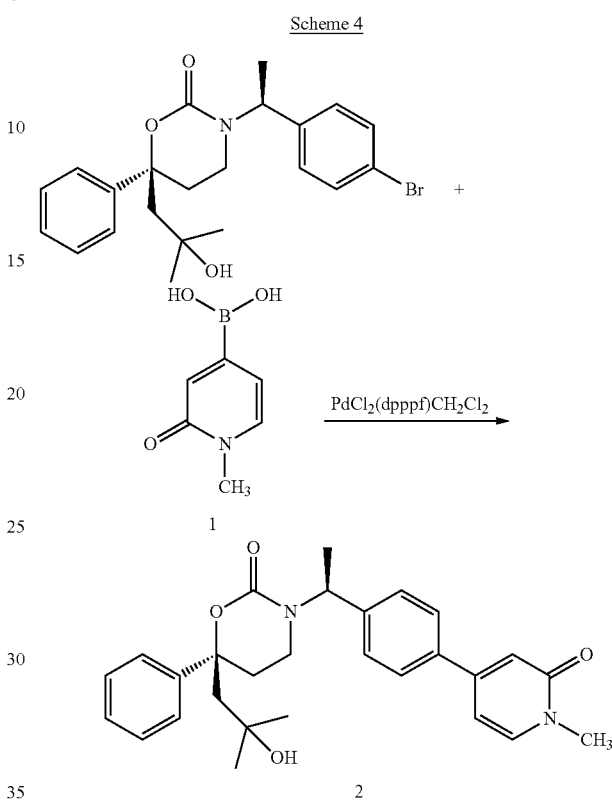

Scheme 4

A reaction flask is charged with (S)-3-((S)-1-(4-bromophenyl)ethyl)-6-(2-hydroxy-2-methylpropyl)-6-phenyl-1,3-oxazinan-2-one (19.66 g, 45.47 mmol) (see Ex. 588 of WO/2009/017664), compound 1 (7.65 g, 50.02 mmol), [1,1'-bis(diphenylphosphino)ferrocene]dichloropalladium(II), complex with dichloromethane (37.40 mg, 0.046 mmol), potassium carbonate (18.85 g, 136.42 mmol) and 2-propanol (100 mL). The flask is evacuated and refilled with argon three times. The contents of the reactor are heated to 80° C. and held for about 6 hours at which time compound 1 is completely consumed. The contents of the reactor are then treated with a solution of N-acetyl-L-cysteine (0.75 g, 4.58 mmol) in 2-propanol (100 mL) and stirred at 80° C. for 2 hours. The resultant suspension is then filtered. (The suspension is maintained at 50° C. to 70° C. during the filtration step.) The resultant solids are then rinsed with 2-propanol (50 mL preheated to 70° C.). The combined filtrate and washes is heated to 70° C., maintained at reduced pressure until about 150 ml of volatiles are removed, cooled to 65° C., and seeded with compound 2. The resultant suspension is stirred at 60-65° C. for 0.5 hours, cooled to 0° C. over about 2 hours, and maintained at 0° C. for 1 hour. The resultant solids are collected by filtration and washed with cold 2-propanol (50 mL). The solids are then recrystallized from a mixture of 2-propanol (40 mL) and water (200 mL) to provide compound 2 (monohydrate) as a white solid. Yield: 19.38 g, 88.2% yield based on BI135541. Purity: 98.96 wt %. Analysis of the product agrees with the data reported in Example 48, Method 2 of WO/2009/134400 which describes the synthesis of the monohydrate of compound 1 by reacting 4-iodo-1-methylpyridin-2(1H)-one with (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one.

What is claimed is:

1. A compound of formula (I):

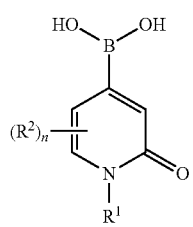

wherein:
n is 0, 1, 2 or 3;
$R^1$ is —$(C_1$-$C_6)$alkyl or —$(C_3$-$C_6)$cycloalkyl; and
each $R^2$ is independently selected from —$(C_1$-$C_6)$alkyl, —$O(C_1$-$C_6)$alkyl, —$(C_3$-$C_6)$cycloalkyl, halo, —$NH_2$, —$NH(C_1$-$C_6)$alkyl, —$N((C_1$-$C_6)$alky)l_2$, and —$CN$.

2. The compound of claim 1, wherein $R^1$ is —$(C_1$-$C_6)$alkyl.

3. The compound of claim 2, wherein $R^1$ is methyl.

4. The compound of claim 1, wherein $R^1$ is —$(C_3$-$C_6)$cycloalkyl.

5. The compound of claim 4, wherein $R^1$ is cyclopropyl.

6. The compound of claim 1, wherein n is 0.

7. The compound of claim 1, wherein $R^1$ is methyl and n is 0.

8. The compound of claim 1, wherein $R^1$ is cyclopropyl and n is 0.

9. A method of making the compound of formula (I) of claim 1, comprising allowing compound of formula (II)

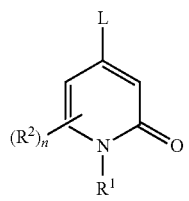

to react with a Grignard reagent of formula $R^3MgX$ to form a first intermediate;
allowing the first intermediate to react with an alkylborate of formula $B(OR^4)_3$ to form a second intermediate; and
hydrolyzing the second intermediate to form the compound of formula (I); wherein
$R^1$, $R^2$ and n are as defined above for the compound of formula (I);
$R^3$ and $R^4$ are each independently a —$(C_1$-$C_6)$alkyl;
L is a leaving group selected from halo and trifluoromethanesulfonyloxy; and
X is a chloro, bromo, or iodo.

10. A method of making a compound of formula (IV), or a hydrate thereof:

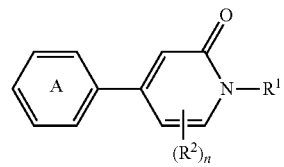

the method comprising:
allowing a compound of formula (I) of claim 1:

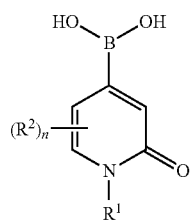

to react with a compound of formula (III):

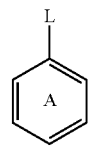

wherein:
ring A in the compound of formula (III) is a $C_{6-10}$ aryl or 5 to 11-membered heteroaryl;
L is a leaving group;
n is 0, 1, 2 or 3;
$R^1$ is —$(C_1$-$C_6)$alkyl or —$(C_3$-$C_6)$cycloalkyl; and
each $R^2$ is independently selected from —$(C_1$-$C_6)$alkyl, —$O(C_1$-$C_6)$alkyl, —$(C_3$-$C_6)$cycloalkyl, halo, —$NH_2$, —$NH(C_1$-$C_6)$alkyl, —$N((C_1$-$C_6)$alky)l_2$, and —$CN$.

11. The method of claim 10, wherein:
the compound of formula (I) is 1-methyl-2-oxo-1,2-dihydropyridin-4-ylboronic acid;
the compound of formula (III) is (S)-3-((S)-1-(4-bromophenyl)ethyl)-6-(2-hydroxy-2-methylpropyl)-6-phenyl-1,3-oxazinan-2-one; and
the compound of formula (IV) is (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one, or a hydrate thereof.

* * * * *